(12) United States Patent
Yau et al.

(10) Patent No.: US 12,390,667 B2
(45) Date of Patent: Aug. 19, 2025

(54) ULTRASONIC TREATMENT OF VITREOUS OPACITIES

(71) Applicants: Sunnybrook Research Institute, Toronto (CA); Vitreosonic Inc., Toronto (CA)

(72) Inventors: Gary Lloyd Ka Tao Yau, North York (CA); Kullervo Henrik Hynynen, Toronto (CA)

(73) Assignees: VITREOSONIC INC., Toronto (CA); SUNNYBROOK RESEARCH INSTITUTE, Toronto (CA)

( * ) Notice: Subject to any disclaimer, the term of this patent is extended or adjusted under 35 U.S.C. 154(b) by 116 days.

(21) Appl. No.: 18/167,602

(22) Filed: Feb. 10, 2023

(65) Prior Publication Data
US 2023/0191162 A1 Jun. 22, 2023

Related U.S. Application Data

(63) Continuation of application No. PCT/US2021/046819, filed on Aug. 20, 2021.
(Continued)

(51) Int. Cl.
*A61N 7/00* (2006.01)
*A61N 7/02* (2006.01)

(52) U.S. Cl.
CPC ........ *A61N 7/02* (2013.01); *A61N 2007/0052* (2013.01)

(58) Field of Classification Search
CPC .............. A61N 7/02; A61N 2007/0052; A61N 2007/0004; A61N 2007/0039;
(Continued)

(56) References Cited

U.S. PATENT DOCUMENTS

| 4,846,172 A | 7/1989 | Berlin |
| 6,679,855 B2 | 1/2004 | Horn et al. |

(Continued)

FOREIGN PATENT DOCUMENTS

| CA | 2873130 A1 | 11/2013 |
| CN | 219000854 U | 5/2023 |

(Continued)

OTHER PUBLICATIONS

Lucas, B. et al., "Ultrasonically Induced Disruption and Hemolysis of Vitreous Hemorrhages", Ultrasound in Med. & BioL vol. 15, No. 1, pp. 29-37, 1989.
(Continued)

*Primary Examiner* — Ashley K Buran
*Assistant Examiner* — Zainab Mohammed Aldarraji
(74) *Attorney, Agent, or Firm* — Stephen Leonard; Aird & McBurney LP

(57) ABSTRACT

At ultrasound intensities below the cavitation threshold of the vitreous and blood cells (e.g., between 0.1 watts per square centimeter ($W/cm^2$) and 3.5 $W/cm^2$), relative hyperthermia can induce temperature elevations that result in hemolysis as well as liquefy vitreous, both of which can accelerate clearance. At high intensities (i.e., >800 W/cm2), with temperatures reaching >100 deg C., the target region may be vaporized. At intensities above the cavitation intensities short ultrasound bursts can result in mechanical fragmentation of the clot. In at least some examples, the present systems, devices and methods will allow for all of these modes of therapies.

25 Claims, 3 Drawing Sheets

Related U.S. Application Data

Figure 1:
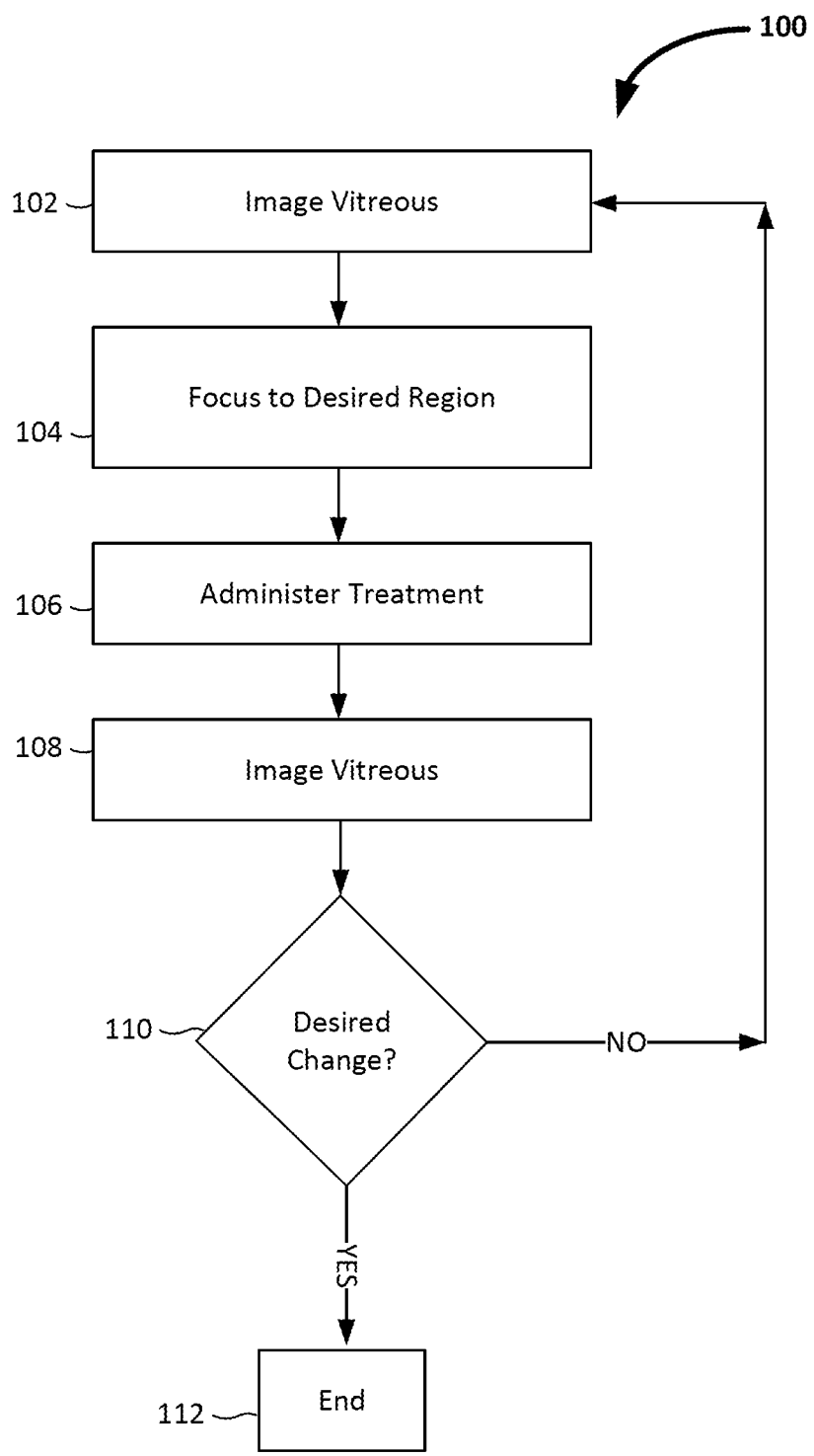

(60) Provisional application No. 63/068,643, filed on Aug. 21, 2020.

(58) Field of Classification Search
CPC .... A61N 2007/0065; A61N 2007/0095; A61B 2090/373; A61B 2090/3782; A61B 2090/378; A61B 8/10; A61B 8/5223; A61F 9/00745

See application file for complete search history.

(56) References Cited

U.S. PATENT DOCUMENTS

| | | | |
|---|---|---|---|
| 8,517,944 B2 | 8/2013 | Peyman | |
| 8,652,073 B2 | 2/2014 | Romano et al. | |
| 8,758,252 B2 | 6/2014 | Eilers et al. | |
| 8,905,949 B2 | 12/2014 | Romano et al. | |
| 9,259,597 B2 | 2/2016 | Romano et al. | |
| 9,403,039 B2 | 8/2016 | Romano et al. | |
| 9,517,359 B2 | 12/2016 | Romano et al. | |
| 9,802,062 B2 | 10/2017 | Bujak | |
| 9,931,245 B2 | 4/2018 | Romano et al. | |
| 10,065,051 B2 | 9/2018 | Bujak | |
| 10,165,941 B2 | 1/2019 | Walsh et al. | |
| 10,603,521 B2* | 3/2020 | Emery | A61N 7/02 |
| 11,097,131 B2 | 8/2021 | Chapuis et al. | |
| 11,241,334 B2 | 2/2022 | Potter, Jr. et al. | |
| 11,701,134 B2 | 7/2023 | Maxwell et al. | |
| 11,839,510 B2 | 12/2023 | Giphart et al. | |
| 11,857,459 B2 | 1/2024 | Suen et al. | |
| 2007/0016039 A1 | 1/2007 | Vortman et al. | |
| 2008/0045865 A1* | 2/2008 | Kislev | A61B 5/411 601/3 |
| 2012/0259250 A1* | 10/2012 | Sapozhnikov | A61B 8/00 601/2 |
| 2013/0006106 A1* | 1/2013 | O'Reilly | A61B 8/0808 600/431 |
| 2013/0197400 A1 | 8/2013 | Romano et al. | |
| 2013/0197633 A1 | 8/2013 | Romano et al. | |
| 2013/0245505 A1 | 9/2013 | Khuri-Yakub et al. | |
| 2014/0074076 A1* | 3/2014 | Gertner | A61B 6/12 606/169 |
| 2016/0022490 A1 | 1/2016 | Ergun et al. | |
| 2016/0157817 A1 | 6/2016 | Tanassi et al. | |
| 2018/0348168 A1 | 12/2018 | Catheline et al. | |
| 2019/0021639 A1* | 1/2019 | Moody | A61B 5/14546 |
| 2019/0105519 A1 | 4/2019 | Herekar et al. | |
| 2020/0164231 A1 | 5/2020 | Cannata et al. | |
| 2020/0330075 A1 | 10/2020 | O'Reilly et al. | |
| 2021/0052416 A1 | 2/2021 | Herekar et al. | |
| 2021/0259880 A1 | 8/2021 | Newton et al. | |
| 2023/0071141 A1 | 3/2023 | Carpentier | |
| 2023/0320899 A1 | 10/2023 | Ootsuki | |

FOREIGN PATENT DOCUMENTS

| | | | |
|---|---|---|---|
| CN | 116919717 A | 10/2023 | |
| FR | 3059224 A | 1/2018 | |
| GB | 2167305 A | 5/1986 | |
| JP | 2015104498 A | 6/2015 | |
| JP | 6460990 B2 | 1/2019 | |
| KR | 20120037180 A | 4/2012 | |
| WO | WO-2017062673 A1 * | 4/2017 | ........... A61B 3/0058 |
| WO | 2018049246 A1 | 3/2018 | |
| WO | 2020116882 A1 | 6/2020 | |
| WO | 2020237382 A1 | 12/2020 | |
| WO | 2021122764 A1 | 6/2021 | |
| WO | 2021122765 A1 | 6/2021 | |
| WO | 2023002227 A1 | 1/2023 | |
| WO | 2023272388 A1 | 1/2023 | |
| WO | 2023081928 A1 | 5/2023 | |

OTHER PUBLICATIONS

Sanghvi N T et al: "New Developments in Therapeutic Ultrasound", IEEE Engineering in Medicine and Biology Magazine, IEEE Service Center, Piscataway, NJ, US, vol. 15, No. 6, Nov. 1, 1996 (Nov. 1, 1996), pp. 83-92, XP000638031, ISSN: 0739-5175, DOI: 10.1109/51.544515.

* cited by examiner

ULTRASONIC TREATMENT OF VITREOUS OPACITIES

CROSS-REFERENCE TO RELATED APPLICATIONS

This application is a continuation of International Application No. PCT/US21/46819, filed Aug. 20, 2021, which claims priority to U.S. Provisional Application Ser. No. 63/068,643, filed Aug. 21, 2020, the disclosure of which is incorporated by reference as if fully set forth herein.

FIELD OF THE DISCLOSURE

The present disclosure relates to devices, systems, and methods for treating vitreous opacities. More particularly, the present disclosure relates to devices, systems, and methods for using ultrasonic waves for treating vitreous opacities.

BACKGROUND OF THE DISCLOSURE

Vitreous hemorrhage (VH) is a common ocular blinding condition. Patients suffering from vitreous hemorrhages that do not naturally resolve are treated surgically. Common surgical methods are invasive and uncomfortable for the patient. Additionally, they may result in infection. Surgical methods are also invasive, so have with them inherent risks, including retinal detachment and infection, both of which if they were to occur, are severe complications that can lead to permanent blindness. Furthermore, currently all vitreous surgery is performed in operating rooms, which increases the cost of the treatment.

Thus, it would be beneficial to develop new non-invasive techniques and devices to treat vitreous hemorrhage.

SUMMARY OF THE DISCLOSURE

In at least some examples, a method of treating an eye, includes (i) imaging a patient's vitreous using a probe, (ii) defining a window on a desired region of the vitreous, (iii) administering ultrasonic energy treatment to the desired region within the window, (iv) continually monitoring the treatment via the probe, (v) adjusting a characteristic of the ultrasonic energy treatment based on the monitoring, (vi) re-imaging the desired region of the vitreous after the treatment is administered, and (vii) evaluating or observing the desired region to determine whether a target percentage of a vitreous opacity has been resolved.

BRIEF DESCRIPTION OF THE DISCLOSURE

Figure 2A:
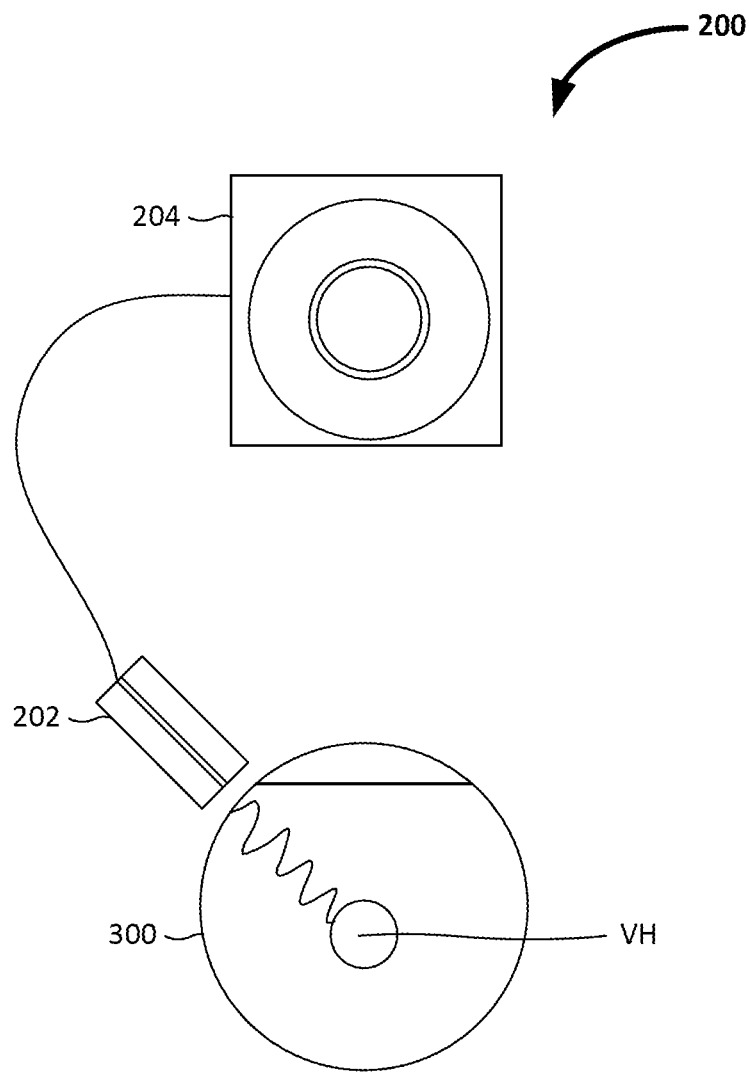
Figure 2B:
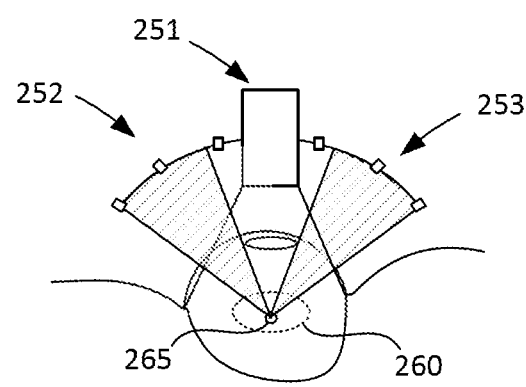
Figure 3:
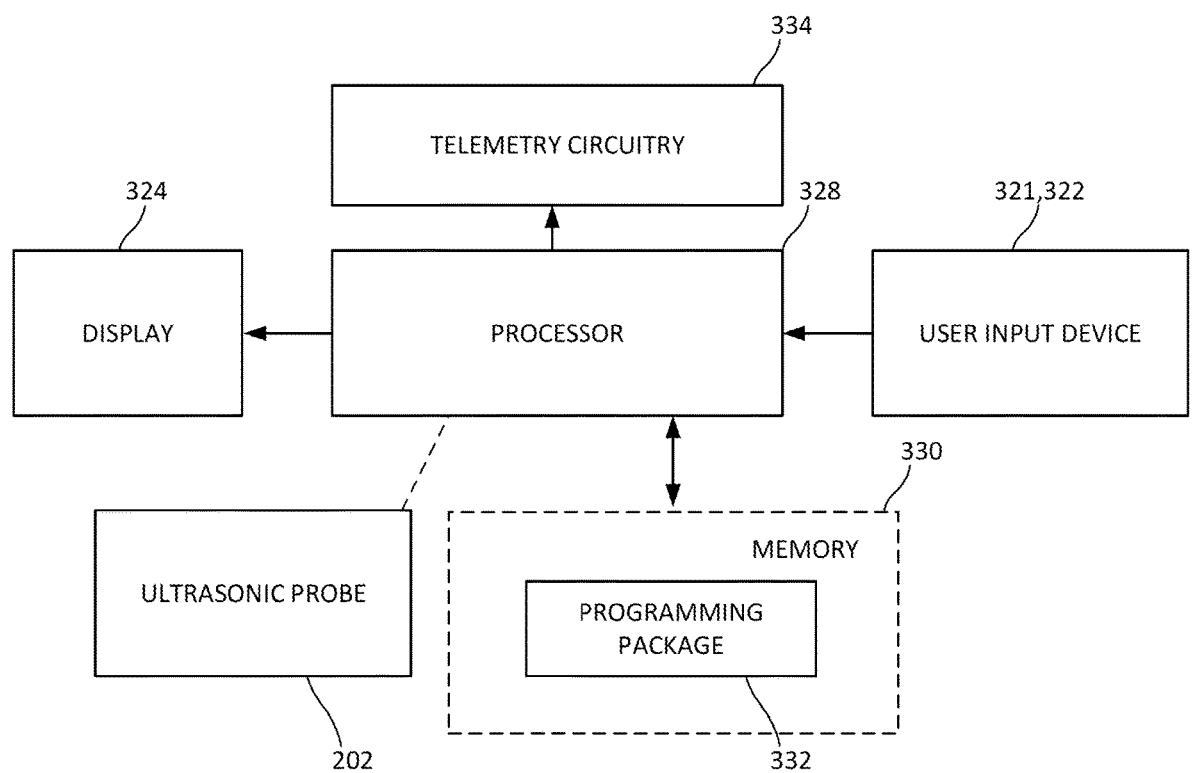

Various embodiments of the presently disclosed devices, systems and methods are shown herein with reference to the drawings, wherein:

FIG. 1 is schematic workflow diagram of a method of treating vitreous hemorrhage;

FIGS. 2A-B are schematic diagram showing components of an ultrasonic device according one embodiment of the present disclosure; and FIG. 3 is a block diagram of the components of a system according to the present disclosure.

Various embodiments of the present invention will now be described with reference to the appended drawings. 1 is to be appreciated that these drawings depict only some embodiments of the invention and are therefore not to be considered limiting of its scope.

DETAILED DESCRIPTION

Despite the various improvements that have been made to systems and methods of treating vitreous hemorrhage, conventional techniques and devices suffer from some shortcomings as described above.

There therefore is a need for further improvements to the devices, systems, and methods of treating vitreous hemorrhage. Among other advantages, the present disclosure may address one or more of these needs.

As used herein, the term "proximal," when used in connection with a component of a probe assembly, refers to the end of the component closest to the physician when the probe is used on a patient, whereas the term "distal," when used in connection with a component of a probe assembly, refers to the end of the component farthest from the physician when the assembly is used on a patient.

Likewise, the terms "trailing" and "leading" are to be taken as relative to the operator (e.g., physician) of the probe assembly. "Trailing" is to be understood as relatively close to the operator, and "leading" is to be understood as relatively farther away from the operator.

It is believed that the rate of vitreous hemorrhage clearance/resorption from the eye can be accelerated by hemolysis, fibrinolysis, increase in local phagocytic activity, and vitreous liquefaction (which involves a breakdown of collagen fibres in the vitreous macrostructure).

In at least some examples, ultrasonic waves may be used in a non-invasive technique to affect at least some of these factors via thermal and/or non-thermal mechanisms, potentially making it a viable treatment modality to accelerate vitreous hemorrhage clearance.

The present systems, method and techniques improve on previous techniques and methods. Specifically, the present disclosure includes an image-guided ultrasonic treatment system for vitreous hemorrhage. In one example, the system contains the ability to modify treatment parameters, combined with a concurrent imaging system providing structural and/or functional information at the time of treatment that can enhance the success of the treatment. For example, as shown in FIG. 1, a method for treating vitreous hemorrhage 100 may include imaging the vitreous 102, focusing on a desired region of the vitreous 104, administering ultrasound non-invasively 106, re-imaging the vitreous after treatment 108, measuring or observing desired changes 110 and repeating the process if the desired change has not occurred, or ending the process 112 if the method has been successful in clearing up the vitreous hemorrhage. In some examples, this step includes structural/direct view, but aided with functional information, such as:

1. direct observation via ultrasound image of the clot.
2. functional measurement of real-time temperature;
3. functional measurement of elasticity; and/or
4. functional measurement of hemoglobin status.

FIG. 2A is a schematic diagram of an exemplary system. Ultrasonic system 200 may include a dual probe 202 that includes a transducer for therapeutic ultrasound probe (0.5 to 10 MHz) and a diagnostic ultrasound probe (5 to 20 MHz) and may include an optical or infrared camera. Probe 202, which can be handheld or fixed in a manual or motorized positioning device, may be applied to a non-transparent portion of the eye 300 (e.g., the sclera), so as to limit exposure of the ultrasonic waves to the cornea and lens. The optical/infrared camera visualizes the eye through the lens.

In some embodiments the ultrasound imaging may be done through the cornea and the lens and in some embodiments the optical imaging is done via optical fiber to minimize the size of the probe. In some embodiments the probe 202 will have one or more ultrasound receivers to detect the scattered ultrasound signals that can be used to control the exposure and/or to monitor the safety and/or to detect the photoacoustic signals. In some embodiments the probe will include an optical fiber to deliver laser pulses into the eye for photoacoustic imaging. In some embodiments the therapeutic ultrasound transducer is a single or multi element fixed focus transducer. The focusing is achieved by overlapping fields, lenses, reflectors, variable path propagation device, or making the transducer curved such as to achieve the desired acoustic focus. In some embodiments the therapy transducer is a phased array that can perform electronic focusing and beam steering. The probe 202 may be in communication with a viewing system 204 for the operator, which displays the corresponding image of the eye. In some examples, the probe 202 is wired to viewing system 204. In at least some other examples, dual probe 202 is wirelessly connected to viewing system 204 via WLAN, Bluetooth or other suitable communications protocol. Once a target is identified on the screen, which corresponds to the vitreous hemorrhage "VH" in the eye, the operator can then initiate the treatment. This process is repeated until the therapeutic endpoints are achieved as described in the process of FIG. 1. In FIG. 2B, an exemplary system is shown of an integrated probe that includes an imaging element 251, ultrasonic detectors 252 and a therapy beam 253. The integrated probe may be disposed and oriented toward a target 260, and the treatment and diagnostic elements may be focused at a certain position 265.

There are at least four ways how ultrasound can be used for the treatment of the hemorrhage. First, it will be appreciated that elevated temperatures can cause hemolysis. Therefore, the highly focused ultrasound can be used to cause a quick, local temperature elevation above the threshold of the cell membrane rupture. Second, high pressure amplitude ultrasound bursts can cause gas bubble formation at the focus. This is called cavitation. The collapse is associated with a shock wave that can disintegrate the cells. Third, longer high-pressure amplitude burst either with or without cavitation can cause the increase the tissue temperature above the water boiling point and cause vaporization. Fourth, ultrasound absorption in medium causes an energy loss from the beam that translates into a radiation force. This radiation force can be used to move fluid or cells noninvasively. Therefore, the radiation force could be used to disperse the clot. Each of these bio-effects can be used either alone or in combination with one or more of the other bio-effects for the treatments of the Vitreous hemorrhages. Vitreous hemorrhage presents in a heterogeneous manner, and hence differing regions require a customized treatment, even within the same eye. For example, thicker clotted blood may require a short pulse of high intensity focused ultrasound to achieve a certain temperature and subsequent ablation to a specified focal region, followed immediately with moderate intensity pulsed radiation force-based treatment to mechanically disperse the clot. Conversely, diffuse non-clotted red blood cells homogeneously mixed within a more liquefied vitreous may be treated with moderate intensity over a longer period over a wider volume, to efficiently elevate the temperature of a wider volume of vitreous to allow for hemolysis, while relying on milder non-thermal mechanisms such as radiation force induced steaming to induce desired changes.

To increase the specificity of the delivery of ultrasonic energy for treatment, a device may be configured to manipulate any one, two, three or four of the parameters described above (i.e., local temperature rise, cavitation, vaporization, radiation and force). Any combination of these parameters may be used to adjust performance of an ultrasonic probe in direct response to the real time monitoring data feedback. In some examples, a focused ultrasound device may choose any of the four parameters, or combination thereof, (e.g., based on a strength or magnitude of the parameter) and adjust the performance of the therapeutic probe accordingly. A therapeutic device may also make adjustments to the performance based on all four, or any combination of the four parameters by utilizing a weighted average or other suitable weighting method. Additionally, to allow for these customized treatments, the current system may allow for real-time adjustments in acoustic output, level of beam focusing, and/or pulsed or continuous treatments depending on the goals of therapy.

At ultrasound intensities below the cavitation threshold of the vitreous and blood cells (e.g., between 0.1 W/cm$^2$ and 3.5 W/cm$^2$), relative hyperthermia can induce temperature elevations that result in hemolysis as well as liquefy vitreous, both of which can accelerate clearance. At high intensities (i.e., >800 W/cm$^2$), with temperatures reaching >100 deg C., the target region may be vaporized. At intensities above the cavitation intensities short ultrasound bursts can result in mechanical fragmentation of the clot. In at least some examples, the present systems, devices and methods will allow for all of these modes of therapies.

Additionally, dynamic electronic or mechanical beam focusing allows for accurate targeting of the region of interest. Without being bound by any particular theory, it is believed that advances in ultrasound transducers allow for dynamic steering that can change the focal point, and hence allow for robust and efficient changes in focusing. This may be advantageous as different regions in the vitreous cavity can then be targeted quickly and in real-time. As an added feature, a computer/processor can "lock-in" to this region on the diagnostic ultrasound to assist the user. This region can be a focal point, and/or a volume. With respect to a volume treatment, the focal area may be defocused enough so as to expand the focal region up to a certain volume.

In some examples, a "volume" treatment may be performed by having the computer lock in to a region, and then subsequent focal and focused treatments in rapid succession within that volume, with the pulses being so short in between that it is seemingly simultaneous or the sonications may be separated by a time interval to allow tissue cooling prior the next sonication. This range can include focal treatment areas or volumetric which can encompass the entire vitreous body.

Using the disclosed method and techniques, the effects may be contained to the region of interest, and not cause any significant biologic effect to non-targeted adjacent tissues. In some examples, the user may manually avoid the non-targeted tissue. Additionally, because the vitreous body has a very distinct imaging characteristic from surrounding features, a computer algorithm may serve as an automatic differentiator as an additional failsafe.

In some examples, continuous treatments will allow for an accumulation of absorption of insonified energy, elevating temperature of the target tissue. Conversely, pulsed treatments can limit temperature accumulation, and hence may be more appropriate for inducing non-thermal effects. Again, this setting will be able to be manipulated in real-time depending on the characteristics of the target region.

To facilitate this customized treatment, an equally advanced diagnostic ultrasound component may accompany the treatment unit. This real-time imaging unit may allow for treatment planning, real time image-guidance and or control during treatment, and visualization of effect on the insonified region.

In addition to the structural changes seen during treatment, including the visualization of the movement of the vitreous, as well as any hypo- or hyper-echoic regions as a result of treatment (which signifies a biologic mechanical effect or cavitation), three additional functional parameters may further assist the operator during the treatment and for subsequent monitoring of progress.

The first functional parameter may include thermography, which includes providing an estimate of the spatial temperature distribution of the insonified region. This can be measured via ultrasound thermography. For this purpose the temperature dependent ultrasound scattering and/or speed of sound or tissue stiffness may be calibrated for temperature estimation.

The second functional parameter is a measure of hemoglobin level and status. Photoacoustic imaging, where a laser light is emitted at a frequency, which is specific to hemoglobin absorption, causing local temperature elevation and thermal expansion that induces an ultrasound signal that can be detected by the receivers in the probe. These signals may be localized and may be used to quantify hemoglobin in the vitreous cavity. Hemoglobin has a specific electromagnetic radiation absorption signature that can be identified via photoacoustic imaging. Further, hemoglobin variants (oxy-hemoglobin and deoxy-hemoglobin) also have distinct electromagnetic absorption characteristics, and the quantification of this can also inform the stage of vitreous hemorrhage. In addition to a real-time display of this information, this measure can provide a means to monitor and/or control effects with sequential therapy.

The third functional parameter is elastography, which is a measure of the stiffness within the vitreous body. The vitreous, particularly with hemorrhage, is a heterogenous space, and presumably varying elasticity of the vitreous opacity may warrant specific treatment requirements. The stiffness changes can be monitored for example by using local harmonic motions methods where the therapy beam is pulsed and the radiation force induced tissue displacement tracked by ultrasound between the short (for example 50 ms) bursts.

To allow the clinician to perform these functions, a system 300 may include additional components such as a mouse 321, a keyboard 322, and a display screen 324. It is to be understood that in addition to, or in lieu of, the mouse 321, other directional programming devices may be used, such as a joystick, touch screen or directional keys included as part of the keys associated with the keyboard 322. As shown in FIG. 3, the system generally includes a processor 328 (e.g., a central processor unit (CPU)) in communication with ultrasonic probe 202 and memory 330 that stores a programming package 332, which can be executed by the processor 328 to allow a clinician to program probe. The system 300 may further include telemetry circuitry 334 for downloading treatment parameters to the probe and uploading treatment data or information to another computer or network. The telemetry circuitry 334 may also be configured for transmitting the control data and receiving status information.

Thus, the described system may provide a non-invasive medical device with the goal of accelerating vitreous hemorrhage clearance. It consists of a customizable platform for therapeutic ultrasound, in combination with real-time ultrasound based diagnostic system providing structural and functional feedback to optimize and/or control the treatment. Additionally, the same or similar systems, methods or devices may be used to diagnose, detect, and/or treat non-hemorrhage opacities or other vitreous opacities. Though the description above has been primarily directed to clearing blood in the eye, this is only exemplary and other methods of treatment of the eye are also contemplated. For example, certain vitreous "floaters," are an aggregation of vitreous macromolecules that are suspended within the vitreous body, which can result in visually disabling symptoms. These vitreous opacities can be resolved using these techniques as well. Thus, the present devices and methods may be used to treat not only vitreous hemorrhage, but also other vision disturbing vitreous opacities.

Although the invention herein has been described with reference to articular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be snared with others of the described embodiments.

What is claimed is:

1. An image-guided ultrasonic system for treating a vitreous opacity in an eye, the system comprising:
   an ultrasonic probe capable of delivering therapeutic focused ultrasound energy and performing imaging according to one or more imaging modalities; and
   control circuitry operatively coupled to said ultrasonic probe, said control circuitry comprising a processor and memory, said memory comprising instructions executable by said processor for performing operations comprising:
      while controlling said ultrasonic probe to deliver the therapeutic focused ultrasound energy to a target region associated with the vitreous opacity within a vitreous of the eye:
         (i) controlling said ultrasonic probe to obtain one or more images;
         (ii) employing the one or more images to determine an adjustment for modifying the therapeutic focused ultrasound energy delivered to the target region, the adjustment being configured to perform one of: (a) changing a mechanism of ultrasound-mediated treatment of the vitreous opacity from one mechanism of ultrasound-mediated treatment of the vitreous opacity to another mechanism of ultrasound-mediated treatment of the vitreous opacity, and (b) modifying relative contributions of two or more mechanisms of ultrasound-mediated treatment of the vitreous opacity employed in combination treatment of the vitreous opacity; and
         (i) controlling said ultrasonic probe such that the adjustment is applied to modify the therapeutic focused ultrasound energy delivered to the target region;
      the mechanisms of ultrasound-mediated treatment being selected from the group consisting of:

a first mechanism of ultrasound-mediated treatment configured to generate a rapid local elevated temperature above a threshold for cell membrane rupture;

a second mechanism of ultrasound-mediated treatment configured to deliver high-pressure amplitude ultrasound bursts capable of generating cavitation and associated shock waves for cell disintegration;

a third mechanism of ultrasound-mediated treatment configured to deliver a high-pressure amplitude ultrasound burst, either with or without cavitation, to cause an increase the tissue temperature above the water boiling point and thereby cause vaporization; and a fourth mechanism of ultrasound-mediated treatment configured such that ultrasound absorption in the vitreous causes an energy loss from an ultrasound beam that results in a radiation force suitable for moving fluid or cells non-invasively.

2. The system according to claim 1 wherein the images provide structural information.

3. The system according to claim 1 wherein the images comprise one or more thermography images that provide an estimate of a spatial temperature distribution of the target region.

4. The system according to claim 1 wherein the images comprise one or more photoacoustic images providing a spatial measure of hemoglobin level and status.

5. The system according to claim 1 wherein the images are processed to monitor changes in stiffness within the vitreous.

6. The system according to claim 1 wherein said control circuitry is configured such that the second mechanism of ultrasound-mediated treatment is characterized by an acoustic intensity between 0.1 and 3.5 watts/cm^2 (W/cm^2).

7. The system according to claim 1 wherein said control circuitry is configured such that the third mechanism of ultrasound-mediated treatment is characterized by an acoustic intensity over 800 W/cm^2.

8. The system according to claim 1 wherein said control circuitry is configured such that the adjustment comprises a change in relative contributions of two or more mechanisms of ultrasound-mediated treatment of the vitreous opacity employed in combination treatment of the vitreous opacity.

9. The system according to claim 1 wherein said control circuitry is configured such that the adjustment comprises one or more of a change in acoustic output, a change in beam focusing, and a change in pulsed vs. continuous delivery of ultrasound energy.

10. The system according to claim 1 wherein said control circuitry is further configured such that steps (i)-(iii) are repeated one or more times.

11. The system according to claim 1 further comprising a display, wherein said control circuitry is configured such that the images are displayed, during treatment, to an operator to facilitate monitoring of a procedure, wherein the adjustment is determined according to input provided by the operator.

12. The system according to claim 1 wherein said control circuitry is configured to process the images to autonomously determine the adjustment according to one or more therapeutic goals.

13. The system according to claim 12 wherein said ultrasonic probe comprises a phased-array ultrasound transducer, and wherein said control circuitry is configured such that the adjustment is applied to dynamically steer the therapeutic focused ultrasound energy within the target region.

14. The system according to claim 12 wherein the images are processed and the adjustment is determined and applied such that the adjustment is perceived to be applied in real-time.

15. The system according to claim 12 wherein at least one therapeutic goal is associated with accelerating vitreous hemorrhage clearance.

16. The system according to claim 12 wherein at least one therapeutic goal is associated with treatment of anon-hemorrhage opacity.

17. The system according to claim 12 wherein at least one therapeutic goal is associated with treatment of an opacity caused by an aggregation of vitreous macromolecules.

18. The system according to claim 1 wherein said ultrasonic probe is configured and controlled such that the images comprise ultrasound images.

19. The system according to claim 1 wherein said ultrasonic probe comprises an optical camera, and wherein said ultrasonic probe is controlled such that the images comprise optical images.

20. The system according to claim 1 wherein said ultrasonic probe comprises an optical energy source suitable for generating photoacoustic signals within the vitreous, and wherein said ultrasonic probe is controlled such that the images comprise photoacoustic images.

21. The system according to claim 1 wherein said ultrasonic probe is supported by a motorized positioning device, and wherein said motorized positioning device is operably coupled to said control circuitry, and wherein said control circuitry is configured to control said motorized positioning device such that a distal function region of said ultrasonic probe is brought into contact with a non-transparent portion of the eye.

22. The system according to claim 1 wherein said ultrasonic probe comprises one or more ultrasonic therapy transducer elements configured for delivering the therapeutic focused ultrasound energy through a non-transparent portion of the eye when said ultrasonic probe is positioned in an operative orientation contacting the eye.

23. The system according to claim 22 wherein said ultrasonic probe further comprises an optical camera configured for performing optical imaging through a transparent portion of the eye when said ultrasonic probe is positioned in the operative orientation contacting the eye.

24. The system according to claim 23 wherein said ultrasonic probe comprises one or more ultrasonic imaging transducer elements configured for performing ultrasound imaging through a transparent portion of the eye when said ultrasonic probe is positioned in the operative orientation contacting the eye.

25. The system according to claim 1 wherein the vitreous opacity is associated with a vitreous hemorrhage, and wherein the one or more images are processed to determine whether or not hemolysis has been induced.

* * * * *